US012678604B2

(12) United States Patent
Jardim Guaré et al.

(10) Patent No.: US 12,678,604 B2
(45) Date of Patent: Jul. 14, 2026

(54) INTRAURETHRAL MEDICATION DOSAGE FORM AND DEVICE

(71) Applicant: INSTITUTO DE PESQUISA, ENSINO, CIÊNCIA E TECNOLOGIA APLICADA—INSTITUTO GALZU, Campos dos Goytacazes (BR)

(72) Inventors: Maria Regina Jardim Guaré, Sorocaba (BR); Cristian Hugo Gil, Buenos Aires (AR)

(73) Assignee: INSTITUTO DE PESQUISA, ENSINO, CIÊNCIA TECNOLOGIA APLICADA, Campos dos Goytacazes (BR)

( * ) Notice: Subject to any disclaimer, the term of this patent is extended or adjusted under 35 U.S.C. 154(b) by 1187 days.

(21) Appl. No.: 17/767,330

(22) PCT Filed: Aug. 18, 2020

(86) PCT No.: PCT/BR2020/050328
§ 371 (c)(1),
(2) Date: Apr. 7, 2022

(87) PCT Pub. No.: WO2021/026628
PCT Pub. Date: Feb. 18, 2021

(65) Prior Publication Data
US 2023/0021407 A1 Jan. 26, 2023

(30) Foreign Application Priority Data
Aug. 15, 2019 (BR) .......................... 102019016950-8

(51) Int. Cl.
*A61M 31/00* (2006.01)

(52) U.S. Cl.
CPC ..... *A61M 31/00* (2013.01); *A61M 2210/1092* (2013.01); *A61M 2210/1096* (2013.01)

(58) Field of Classification Search
CPC .. A61M 2210/1089; A61M 2210/1092; A61M 2210/1096; A61M 2005/3142;
(Continued)

(56) References Cited

U.S. PATENT DOCUMENTS 2,902,034 A * 9/1959 Simmonds ........ A61M 5/31513
604/222
6,159,184 A * 12/2000 Perez .................. A61M 5/3271
604/234
(Continued)

FOREIGN PATENT DOCUMENTS

| GB | 1321920 A | 7/1973 |
|----|-----------|--------|
| WO | 9628142 A1 | 9/1996 |
| WO | 2017082792 A1 | 5/2017 |

*Primary Examiner* — Nilay J Shah
(74) *Attorney, Agent, or Firm* — Laurence P. Colton; Smith Tempel Blaha LLC

(57) ABSTRACT

An intraurethral dosage form of liquid or gel medication for men or women. In one embodiment, an applicator provides advantages in its use, facilitating the application of pharmaceutical compositions directly into the urethral channel and providing fast local effect without substantial risk. The invention provides a dosage form and route of administration for several medications, being particularly useful for the application of anti-inflammatory and/or anesthetic medications, for the treatment of female cystitis, for modulating female genital sensitivity and/or for modulating the erectile function in man, being an advantageous dosage form alternative to the oral or injectable administration of medications or even the intraurethral administration of pills.

11 Claims, 3 Drawing Sheets

(58) Field of Classification Search
    CPC ........ A61M 5/3137; A61M 2005/3139; A61M
                2210/167; A61M 2005/2407; A61M
                5/31591; A61M 5/14244
    See application file for complete search history.

(56)                    References Cited

U.S. PATENT DOCUMENTS

| | | | |
|---|---|---|---|
| 6,500,440 | B1 | 12/2002 | Chi |
| 9,056,044 | B2 | 6/2015 | Mo et al. |
| 9,248,127 | B2 | 2/2016 | Perman et al. |
| 2008/0287879 | A1 | 11/2008 | Harkins |
| 2009/0312707 | A1* | 12/2009 | Bishop .................... A61M 5/24 |
| | | | 604/135 |
| 2016/0271253 | A1 | 9/2016 | Chang |
| 2019/0046726 | A1* | 2/2019 | Naygauz ............... A61J 1/1481 |

\* cited by examiner

INTRAURETHRAL MEDICATION DOSAGE FORM AND DEVICE

FIELD OF THE INVENTION

The present invention is pursuant to the fields of Pharmacy and Medicine. More specifically, the invention provides an intraurethral dosage form of liquid or gel medication for men or women. In one embodiment, an applicator provides advantages in its use, facilitating the application of pharmaceutical compositions directly into the urethral channel and providing fast local effect without substantial risk. The invention provides a dosage form and route of administration for several medications, being particularly useful for the application of anti-inflammatory and/or anesthetic medications, for the treatment of female cystitis, for modulating female genital sensitivity and/or for modulating the erectile function in men, being an advantageous dosage form alternative to the oral or injectable administration of medications or even the intraurethral administration of pills.

BACKGROUND OF THE INVENTION

Dosage forms providing routes of administration for various medications are known and available. However, there are several medical conditions that require therapeutic intervention that still suffer from the lack of options for dosage forms that provide risk reduction, better therapeutic effect, greater ease of use, lower dose, among other technical limitations. The present invention aims to meet this important need by solving these and other technical problems.

Among the various medical conditions that may benefit from the present invention are those in which intraurethral medication administration still has limited dosage form options. Among these, special emphasis is given to anti-inflammatory therapies; anesthetic therapies; treatment of female cystitis or modulation of female genital sensitivity; therapies that modulate erectile function in men, among others.

In this context, INTRACAVERNOUS INJECTIONS with phentolamine, papaverine, and alprostadil are considered second-line treatment for erectile dysfunction, although alprostadil is more commonly used. Intracavernous therapy is also often effective in erectile dysfunction refractory to treatment with oral PDE5 inhibitors, especially in postradical prostatectomy patients. Despite these benefits, intracavernous therapy is an invasive procedure that is associated with 40% to 50% dropout rates due to pain, priapism, penile fibrosis, hematoma, ecchymosis, or needle fear (Anaissie, J. & Hellstrom, W. J. (2016)). Clinical use of alprostadil topical cream in patients with erectile dysfunction: a review. Research and reports in urology, 8, 123-131. doi: 10.2147/RRU.S68560).

A comparative study in 103 unselected patients with erectile dysfunction between MUSE™ (INTRAURETHRAL TABLET of up to 1000 µg Alprostadil and Intracavernous Prostavasin up to 20 µg provided total responses of 43% (MUSE™) vs 70% (Prostavasin™)). Complete penile erections were achieved in 10% (MUSE™) vs 48% (Prostavasin™). In terms of side effects, the penile pain/burn rate reported after MUSE™ was 31.4%, compared to 10.6% after recovery i.c. Alprostadil. Urethral hemorrhage after MUSE™ application was noted in 4.8% In addition, Alprostadil remains the "Gold Standard" in the treatment of male impotence, but MUSE™ should be reserved for a subset of patients suffering from dysfunction (PORST, H. Transurethral alprostadil with MUSE™ (medicated urethral system for erection) vs intracavernous alprostadil—a comparative study in 103 patients with erectile dysfunction. International journal of impotence research, v. 9, n. 4, p. 187, 1997).

Another study with 60 patients (31 Alprostadil and 29 placebo) applying 1% alprostadil+5% SEPA CREAM, improved vaginal penetration 12/31 (39%) with alprostadil versus 2/29 (7%) with placebo, P<0.005 (Goldstein I, Payton T R, Schechter P J. A double-blind, placebo-controlled, efficacy and safety study of topical gel formulation of 1% alprostadil (Topiglan) for the in-office treatment of erectile dysfunction. Urology. 2001; 57(2):301-305).

Another study with 1,732 patients (1,298 alprostadil, 434, placebo) applying CREAM of 100, 200, or 300 µg of alprostadil, had positive results: 12%—placebo, 46%—100 µg, 62%—200 µg, 67%—300 µg, with a discontinuation rate of 2.7% (Padma-Nathan H, Yeager JL. An integrated analysis of alprostadil topical cream for the treatment of erectile dysfunction in 1732 patients. Urology. 2006; 68(2):386-391).

External application of GEL with 1% alprostadil+5% SEPA, in another study with 48 patients, demonstrated a positive correlation with erectile response, as 67 to 75% of patients had an erection compared to 17% of controls (p<0.001). Blood pressure and heart rate varied minimally. No severe adverse event was observed in 48 patients, although most reported skin discomfort (MCVARY, KEVIN T. et al. Topical prostaglandin E1 SEPA* gel for the treatment of erectile dysfunction. The Journal of urology, v. 162, n. 3, p. 726-730, 1999). In this case, patents already provide a local preparation composition containing alprostadil with excellent skin permeation rate and little skin irritation (CHI, Sang-Cheol; LEE, Dong Soo; LEE, Kye Kwan. Topical preparation of alprostadil for the treatment of erectile dysfunction. U.S. Pat. No. 6,500,440, Dec. 31, 2002).

It is noted that there is a clear trend of increasing demand for therapies with local treatments in cream or gel, such as Alprostadil, due to the systemic effects of conventional oral therapies, or due to the side effects of intracavernous injections. However, burning, local irritation, pain or injuries in the urethra are a limiting factor in the use of urethral pills, with a high dropout rate.

The local application of medications against erectile dysfunction has many advantages over their oral counterparts since the systemic effect of actives such as Sildenafil or Tadalafil may cause significant problems for patients. Sildenafil is metabolized by liver enzymes and excreted by the liver and kidneys at doses between 25 and 100 mg/dose. Oral administration of this type of medication may cause problems such as headaches, vision problems, blurred vision, visual disturbances, hot flashes, tachycardia, palpitation, convulsion, fainting, priapism, etc., which are quite common with the use of systemic medications. such as Sildenafil or Tadalafil, among others. The present invention provides a solution to these problems.

The administration of medications in URETHRAL ROUTE is already known practice for some medical conditions, including, but not limited to, anesthetics such as gel xylocaine—used as an anesthetic for medical procedures such as cystoscopy, catheterization, probe exploration and others.

It is known that the intraurethral route requires a lower dosage of the medication, because the medication is already at the site of action, in addition to preserving the body during medication metabolism (liver and kidneys). It is also known that the intraurethral route provides fast absorption, around 10 minutes, to produce effects. However, many dosage forms that provide self-administration of medications in the urethra, which are simple in structure, easy to use by users (patients or health professionals) and/or that are disposable, to increase safety in use, are not yet available. The present invention provides a solution to these technical problems.

Searching in the prior art have revealed documents only partially relevant to the present invention, as none of them anticipates or suggests any of its objects. In the researched literature, no documents were found anticipating or suggesting the teachings of the present invention, so that the solution proposed here, in the judgement of the inventor, has novelty and inventive step compared to the state of the art.

SUMMARY OF THE INVENTION

It is one of the objects of the invention to provide a single dosage form that provides advantages in intraurethral administration of medications. Among the various advantages and technical problems solved by the present invention, the following stand out: the reduction of side effects associated with the conventional treatments currently available; the practicality of use both by the patient (self-administration) and by the healthcare professional; greater safety and comfort; reducing the amount of pharmaceutical active ingredient required for therapeutic action, expanding the therapeutic window and reducing toxicity.

The present invention solves this and other problems by providing an intraurethral medication dosage form comprising a single dose of pharmaceutical composition in liquid or gel comprising: one or more anti-inflammatories; one or more anesthetics; one or more active ingredients for the treatment of female cystitis; one or more active ingredients to modulate female genital sensitivity; one or more active ingredients to modulate erectile function in men; or combinations thereof.

In one embodiment, the single dosage form of the invention comprises a formulation containing between 250 to 1000 mcg of Alprostadil and provides the desired therapeutic effects with a systemic effect approximately 1000 times less than conventional therapy with the same active ingredient, facilitating the clearance of the product and reducing toxicity and the potential for side effects.

In one embodiment, the single dosage form comprises an intraurethral applicator device of liquid or gel composition that provides easy self-administration, providing more comfort and reducing risks.

It is, therefore, another object of the present invention, an intraurethral medication applicator in liquid or gel form comprising:

a receptacle (10), comprising:
    two concave and opposite faces (11) and (12) dockable, inside which there is a space for a plastic syringe, the concave face (11) comprising a groove (13) for fitting the back part of the syringe;
    a rod (14) for displacing the plunger of a syringe (15); and
    a dedicated, disposable, plastic syringe.

In one embodiment, said device further comprises one or more of the following aspects: the plastic syringe is of the extended Luer-Slip type; a cap (17) for the syringe, dedicated, extended Luer-Slip type; a limiter for use in the female urethra (20); four latches (19) of two types, which can make the applicator housing reusable or disposable.

In one embodiment, the concave face (12) of said device comprises a hollow region (16) to provide a view of the contents of the syringe within the receptacle.

In one embodiment, one or both of the external parts of the concave faces comprise shoulders (18) to facilitate use, prevent slipping (grip).

It is another object of the invention, a method for dosing medication, from the intraurethral dosage applicator device, wherein the method comprises at least one of the steps of:

positioning the syringe (15), previously filled with a single dose of the medication and/or fillable at the time of application, in the receptacle (10) of the device; and/or
  actuation of the rod (14) that displaces the plunger of the syringe (15), which contains a single dose of the medication, dispensing the medication.

These and other features of the present patent application will be immediately appreciated by those skilled in the art and by companies with interests in the segment, and will be described in sufficient detail for their reproduction in the following description.

BRIEF DESCRIPTION OF DRAWINGS

The following detailed description and the attached figures illustrate the main features of the present invention, presented in detail to better support the skilled in the art, so that he can understand and reproduce the invention in its various forms of embodiment.

DETAILED DESCRIPTION OF THE INVENTION

Figure 1:
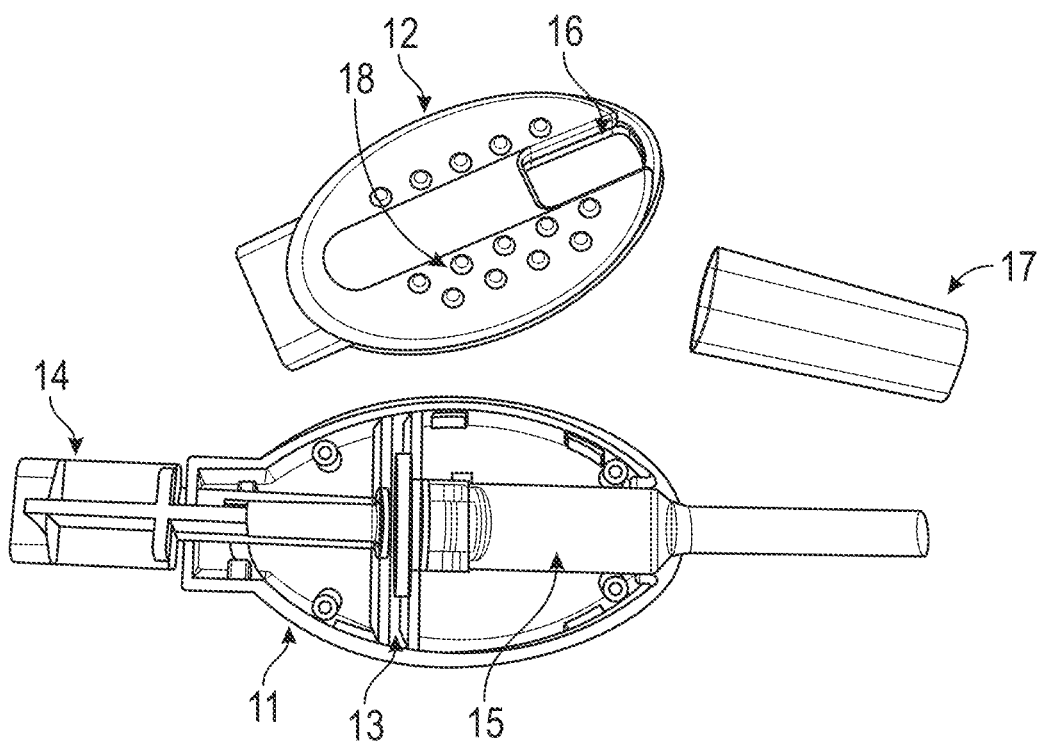
FIG. 1 shows a photo of one embodiment of applicator device, shown open with its internal configuration. The following are indicated: two concave and opposite faces (11) and (12) dockable, the concave face (11) comprising a groove (13) for fitting the back part of the syringe; the rod (14) for displacing the plunger of a syringe. Also shown on the concave face (12) is the hollow region (16) for providing a view of the contents of the syringe within the receptacle and a cap (17) for the syringe tip; shoulders (18) to facilitate use and prevent slipping. Internally, four latches (19) are shown that can make the applicator housing reusable or disposable.

The present invention solves several technical problems by providing an intraurethral medication dosage form comprising a single dose of pharmaceutical composition in liquid or gel comprising: one or more anti-inflammatories; one or more anesthetics; one or more active ingredients for the treatment of female cystitis; one or more active ingredients to modulate female genital sensitivity; one or more active ingredients to modulate erectile function in men; or combinations thereof.

Among the various advantages and technical problems solved by the present invention highlights: the reduction of side effects associated with currently available conventional treatments; the practicality of use by both the patient (self-administration) and the health professional; greater safety and comfort; reducing the amount of pharmaceutical active required for therapeutic action, expanding the therapeutic window and reducing toxicity.

For purposes of the present invention the following definitions are used:

Pharmaceutical Composition

In the context of the present patent application, "pharmaceutical composition" should be understood as any composition that contains an active ingredient, with prophylactic, palliative and/or curative purposes, for urethral administration. In addition to the dosage form of the invention being useful in the administration of various active ingredients, it includes anti-inflammatory and/or anesthetic ones, for the treatment of female cystitis, for modulating female genital sensitivity and/or for modulating erectile function in men.

Pharmaceutically Acceptable Formulation

In the context of the present patent application, "pharmaceutically acceptable formulation" is to be understood as a formulation containing pharmaceutically acceptable excipients and carriers well known to those skilled in the art, such as the development of convenient doses and treatments for use in particular compositions that can be described in a number of urethral treatment regimens. Particularly useful excipients and carriers in the context of the present invention include those for liquid or gel dosage forms.

Applicator Device

In the context of the present patent application, "application device" is to be understood as a device that provides intraurethral administration of pharmaceutical composition in liquid or gel form. Preferably, the coloring of the intraurethral applicator is associated with the medication to be administered, such as: Blue for modulators of erectile function; Orange for anti-inflammatories; Green for anesthetics; Pink for antiseptics in the treatment of female cystitis or modulation of genital sensitivity; among other associations, and can be presented as an individual disposable option or kits according to the form of administration.

Example 1—Alprostadil Dosage Form

Previous comfort tests for self-application were performed on 25 patients, using the intraurethral device described in example 2, filled with 0.25 cm³ of saline. The test results indicated that there was no handling difficulty.

In one embodiment, the single dosage form of the invention comprises a formulation containing between 250 to 1000 mcg of Alprostadil. This dosage form provided the desired therapeutic effects with a systemic effect approximately 1000 times less than conventional therapy with the same active ingredient, facilitating the clearance of the product and reducing the toxicity and potential for side effects.

Example 2—Applicator Device for Use in Men

This embodiment of the present invention is described below with reference to the figures.

FIG. 1 shows a photo of an applicator device embodiment, shown open with its internal configuration. The following are indicated: two concave and opposite faces (11) and (12) dockable, the concave face (11) comprising a groove (13) for fitting the back part of the syringe; the rod (14) for displacing the plunger of a syringe. Also shown on the concave face (12) is the hollow region (16) to provide a view of the contents of the syringe within the receptacle and a cap (17) for the syringe tip. Internally, four latches (19) are shown that can make the applicator housing reusable or disposable. It should be noted that in one embodiment there is a latch that prevents the device from opening after closing. In another embodiment the device can be opened with a snap latch. It should also be noted that said concave faces (11 and 12) comprise a domed perimeter, to facilitate the grip of the device during application.

Figure 2:
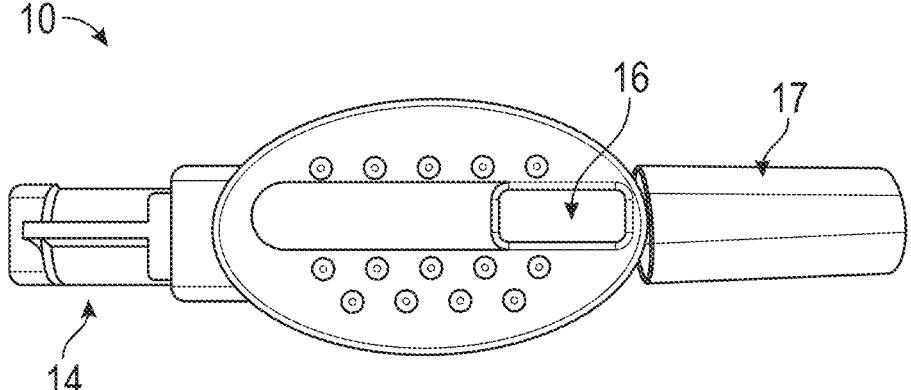
FIG. 2 shows a photo of the same embodiment of the applicator device of FIG. 1, shown in perspective and assembled ready for use. The following are indicated: the receptacle (10) formed by the junction of the concave faces (11 and 12); the back part of the rod (14); the hollow region (16) on the concave face (12); the plastic syringe tip covered by a removable cap (17); and the shoulders (18) to facilitate use, prevent slipping (grip).
Figure 3:
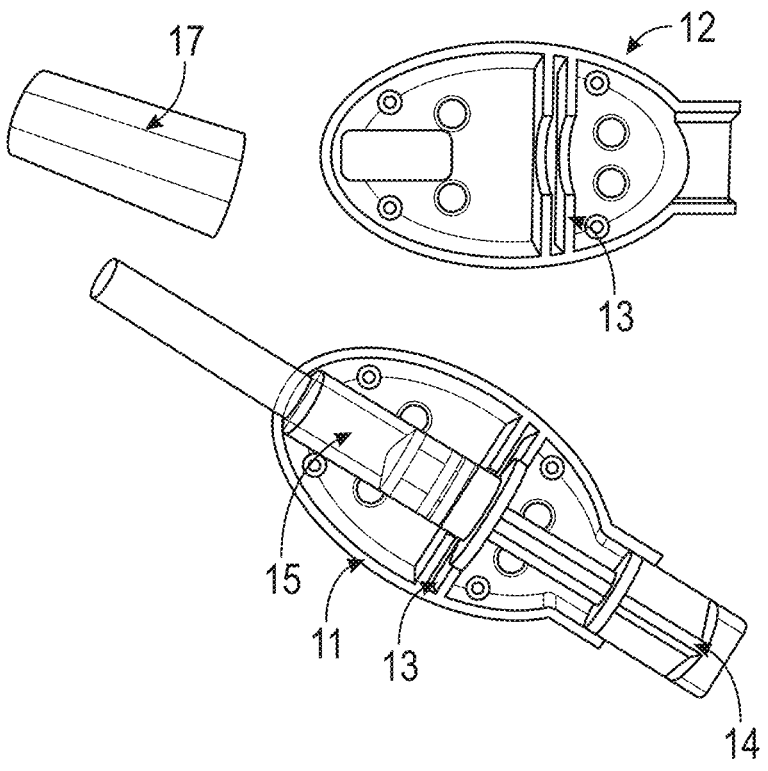
FIG. 3 shows another view of the photo of FIG. 1, showing in greater detail the back part of the concave face (11), indicating the existence of the groove (13) on this face as well.

FIG. 2 shows a photo of the same embodiment of the applicator device of FIG. 1, shown in perspective and assembled ready for use. The following are indicated: the receptacle (10) formed by the junction of the concave faces (11 and 12); the back of the rod (14); the hollow region (16) on the concave face (12); the plastic syringe tip covered by a removable cap (17); and the shoulders (18) to facilitate use, prevent slipping (grip).

Figure 4:
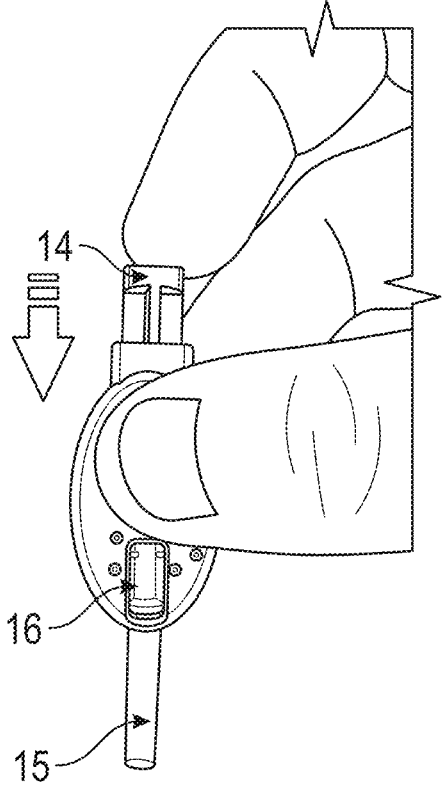
FIG. 4 shows a photo of an embodiment of the application and dosage form of the device shown in FIGS. 1 to 3, which details the activation of the rod (14) with the user's own finger, which moves the syringe plunger (15), and can also check the amount of medication through the hollow region (16).

In the embodiment of FIGS. 1 to 4, the disposable plastic syringe has a volume of 0.25 cm³ and is pre-filled with a single dose of pharmaceutical composition in liquid or gel for application in the urethra. The user does not handle needles or sharp materials and, due to the limited length of the syringe tip, it penetrates the urethra just enough to provide administration pharmaceutical composition by activating the rod (14) that displaces the plunger of the syringe (15), as shown in FIG. 4. Still referring to FIG. 4, it is noted that the user applies the pharmaceutical composition in a simplified way and with good grip of the device, from the domed perimeter and the concavities of the faces (11 and 12), in addition to the shoulders (18) creating a zone of greater friction.

After pressing the plunger and administering the pharmaceutical composition into the urethra, the user can: discard the set when the applicator comes with latches (single use—disposable) or can change the inner syringe when the applicator comes without latches (multiple use—previously prepared syringes in the set kit that will be discarded later).

Figure 5:
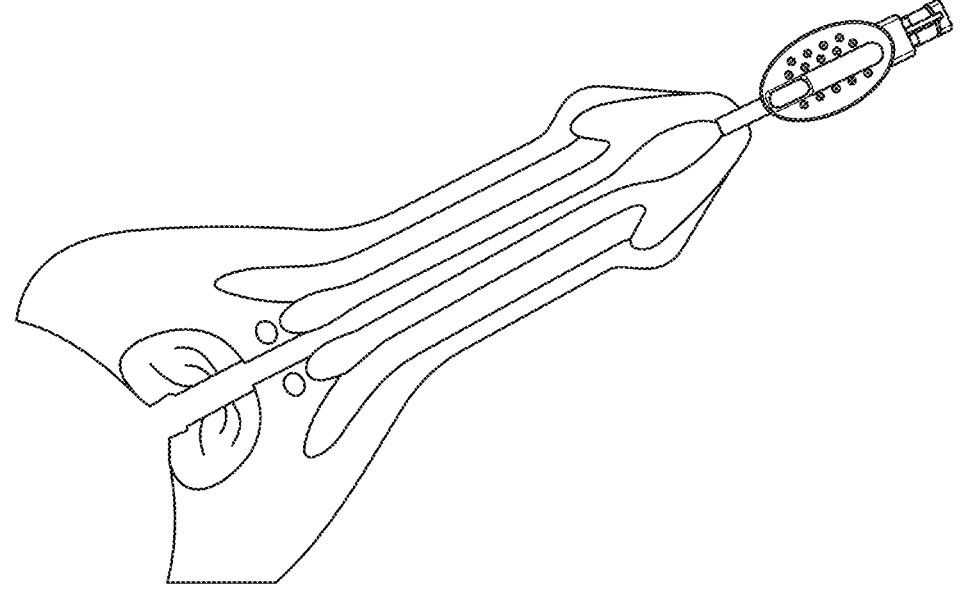
FIG. 5 shows an exemplification of the device applying the single intraurethral dosage of the medication to the penis.

The plastic tip of the syringe is placed in the urethra, penetrating 1 to 2 cm at the tip of the penis, as shown in FIG. 5. The user pushes the plunger administering the medication and then withdraws the intraurethral applicator by gently compressing the distal urethra while in a gliding motion spreads the medication to the base of the penis.

Example 3—Applicator Device for Use in Women

Figure 6:
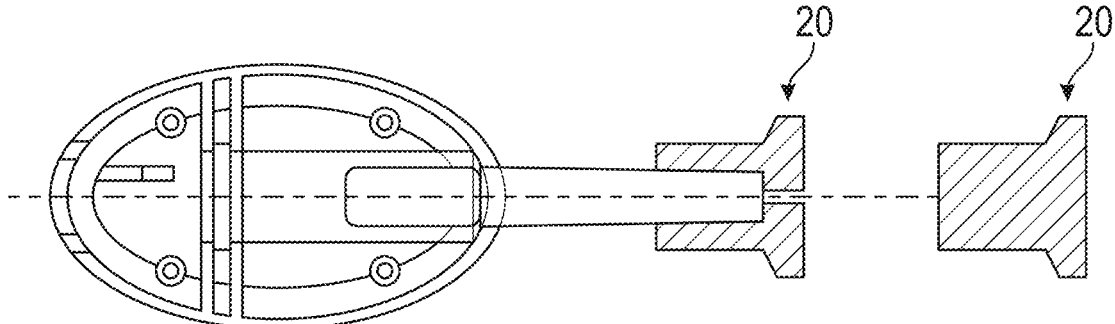
FIG. 6 shows a schematic drawing of one embodiment of an applicator device similar to that described in FIGS. 1 and 5, but for use in the female urethra, with the course limiter (20) for the female urethra, made of silicone for authorized use in humans.

FIG. 6 shows a schematic drawing of an applicator device embodiment similar to that described in FIGS. 1 and 2, but for use in the female urethra, with the course limiter (20) for the female urethra, made of silicone for use authorized in humans.

In this embodiment the disposable plastic syringe is 0.25 cm³ in volume and is pre-filled with a single dose of pharmaceutical composition in liquid or gel for application to the urethra. The user does not handle needles or sharp materials and, due to the travel limiter (20) for the female urethra, it provides the administration of the pharmaceutical composition by activating the rod (14) that moves the plunger of the syringe (15).

The plastic tip of the syringe has a limiter (20) that is lightly pressed around the urethra while the medication is applied gradually. After application, it is recommended to keep the device in place for a few seconds so that reflux does not occur. After removing the device, it is recommended to do a gentle massage until the urinary flow is released.

The silicone limiter (20) that is placed on the tip of the syringe helps the delivery of the formulation in the female urethra, by light compression, without the need to insert the tip of the device.

The device can also be used to deliver small amounts of the medication directly into the urethra, as in cases of localized infections and analgesia.

The single dosage form of the invention is suitable for analgesic, antiseptic, local antibiotic and anti-inflammatory treatment for cases of acute cystitis and other conditions that require local application of medications, without having to resort to parenteral application.

The invention disclosed and exemplified in one or more ways was treated as an industrial secret and was not previously disclosed until the time of filing this patent application. This industrial secret is the depositor's intangible asset. The eventual future publication of the patent application does not, in itself, constitute authorization for use by third parties, serving only as: (i) making third parties aware of the existence of said industrial secret on the filing date; (ii) unequivocal indication of its holder; and (iii) encouraging the development of new improvements based on the concept revealed herein, to avoid reinvestment in the development of the same asset already held by the depositor.

It is immediately noted that any commercial use requires authorization from the holder and that unauthorized use entails sanctions provided for by law. In this context, it is immediately clarified that from the disclosure of the present invention, those skilled in the art may consider other forms of implementing the invention not identical to those merely exemplified above, but that in the event of intended commercial use such forms may be considered as being within the scope of the appended claims.

The invention claimed is:

1. A system for intraurethral medication dosage comprising an intraurethral applicator device and a single dose of liquid or gel pharmaceutical composition comprising one or more anti-inflammatories, one or more anesthetics, one or more active ingredients for the treatment of female cystitis, one or more active ingredients to modulate female genital sensitivity, one or more active ingredients to modulate erectile function in men, or combinations thereof, the single dose being administered by the intraurethral applicator device comprising:

two concave and opposite faces (11, 12) dockable, configured to be held by finger and attached to each other, defining an interior space of a receptacle (10) housing a syringe that is disposable and made of plastic, wherein, the syringe is configured for needle-free intraurethral medication;

one of the concave faces (11) comprises a groove (13) positioned on an internal surface of the interior space of the receptacle (10), where a back part of the syringe enters the groove (13) to be fitted into the interior space of the receptacle (10), wherein the back part of the syringe receives a rod (14) that is configured to displace a plunger (15) of the syringe, releasing the single dose through a tip of the syringe; and the groove (13) comprises two walls, each of the walls having a curved region, wherein the back part of the syringe is fitted between the walls on the curved region.

2. The system for intraurethral medication dosage according to claim 1, further comprising one or more of the following aspects: the plastic syringe is of the extended Luer-Slip type; a cap (17) for the syringe; a limiter (20); four latches (19).

3. The system for intraurethral medication dosage according to claim 1, further comprising a hollow region (16) on another one of the concave faces (12).

4. The system for intraurethral medication dosage according to claim 1, wherein one or both of the concave faces are provided with external parts comprising shoulders (18).

5. The system for intraurethral medication dosage according to claim 1, wherein the syringe comprises the tip disposed in a forward part of the syringe, outside the receptacle (10), and a barrel disposed inside the receptacle (10), wherein the barrel and the tip form a single body.

6. An intraurethral medication dosage device comprising:

two concave and opposite faces (11, 12) dockable, configured to be held by finger and attached to each other, defining an interior space of a receptacle (10) housing a syringe that is disposable, made of plastic, and configured for needle-free intraurethral medication, wherein one of the concave faces (11) comprises a groove (13) positioned on an internal surface of the interior space of the receptacle (10), where a back part of the syringe enters the groove (13) to be fitted into the interior space of the receptacle (10), wherein the back part of the syringe receives a rod (14) that is configured to displace a plunger of the syringe, releasing the single dose thorough a tip of the syringe, and the groove (13) comprises two walls, each of the walls having a curved region, wherein the back part of the syringe is fitted between the walls and on the curved region.

7. The device according to claim 6, characterized in thatwherein another one of the concave faces (12) comprises a hollow region (16) providing a view of the contents of the syringe inside the receptacle (10).

8. The device according to claim 7, further comprising a travel limiter for use in a female urethra (20).

9. The device according to claim 6, wherein the syringe comprises the tip disposed in a forward part of the syringe, outside the receptacle (10), and a barrel disposed inside the receptacle (10), wherein the barrel and the tip form a single body.

10. A method for dosing medication from an intraurethral dosage applicator device, characterized for comprising an administration of a single dose of pharmaceutical composition in liquid or gel form comprising one or more anti-inflammatories, one or more anesthetics, one or more active ingredients for the treatment of female cystitis, one or more active ingredients to modulate female genital sensitivity, one or more active ingredients to modulate erectile function in men, or combinations thereof, wherein the device comprises:

two concave and opposite faces (11, 12) dockable, configured to be held by finger and attached to each other, defining an interior space of a receptacle (10) housing a syringe that is disposable and configured for needle-free intraurethral medication, wherein one of the concave faces (11) comprises a groove (13) positioned on an internal surface of the interior space of the receptacle (10), where a back part of the syringe enters the groove (13) to be fitted into the interior space of the receptacle (10), wherein the back part of the syringe receives a rod (14) and is connected to a plunger (15) of the syringe, wherein the method comprises a step of actuation of the rod (14) that displaces the plunger (15) of the syringe, which contains the single dose of the medication, dispensing the medication through a tip of the syringe; and the groove (13) comprises two walls, each of the walls having a curved region, wherein the back part of the syringe is fitted between the walls on the curved region.

11. The method according to claim 10, further comprising a step of:

positioning the syringe, previously filled with the single dose of the drug and/or fillable at a time of application, in the receptacle (10) of the device.

\*   \*   \*   \*   \*